US009139792B2

(12) United States Patent
Bredsguard et al.

(10) Patent No.: US 9,139,792 B2
(45) Date of Patent: Sep. 22, 2015

(54) PROCESSES OF PREPARING ESTOLIDE BASE OILS AND LUBRICANTS THAT INCLUDE TRANSESTERIFICATION

(71) Applicant: BIOSYNTHETIC TECHNOLOGIES, LLC, Irvine, CA (US)

(72) Inventors: Jakob Bredsguard, Lake Forest, CA (US); Travis Thompson, Anaheim, CA (US)

(73) Assignee: Biosynthetic Technologies, LLC, Irvine, CA (US)

( * ) Notice: Subject to any disclaimer, the term of this patent is extended or adjusted under 35 U.S.C. 154(b) by 253 days.

(21) Appl. No.: 13/875,172

(22) Filed: May 1, 2013

(65) Prior Publication Data

US 2013/0324754 A1 Dec. 5, 2013

Related U.S. Application Data

(60) Provisional application No. 61/655,364, filed on Jun. 4, 2012.

(51) Int. Cl.

| | |
|---|---|
| ***C07C 59/147*** | (2006.01) |
| ***C10M 105/36*** | (2006.01) |
| ***C10M 105/40*** | (2006.01) |
| ***C10M 177/00*** | (2006.01) |
| ***C11C 3/00*** | (2006.01) |
| ***C11C 3/04*** | (2006.01) |

(52) U.S. Cl.

CPC ........... *C10M 105/36* (2013.01); *C10M 105/40* (2013.01); *C10M 177/00* (2013.01); *C11C 3/003* (2013.01); *C11C 3/04* (2013.01); *C10M 2207/2825* (2013.01); *C10M 2207/301* (2013.01); *C10N 2220/024* (2013.01); *C10N 2230/02* (2013.01); *C10N 2230/10* (2013.01); *C10N 2270/00* (2013.01)

(58) Field of Classification Search

CPC .................................................... C08F 210/14
USPC ........................................................ 554/122
See application file for complete search history.

(56) References Cited

U.S. PATENT DOCUMENTS

| | | | | | |
|---|---|---|---|---|---|
| 5,427,704 | A * | 6/1995 | Lawate | ......................... | 508/491 |
| 5,451,332 | A | 9/1995 | Lawate | | |
| 6,018,063 | A | 1/2000 | Isbell et al. | | |
| 6,316,649 | B1 | 11/2001 | Cermak et al. | | |
| 8,580,985 | B2 | 11/2013 | Thompson et al. | | |
| 8,586,771 | B1 | 11/2013 | Lutz et al. | | |
| 2010/0120643 | A1 | 5/2010 | Brown et al. | | |
| 2011/0213170 | A1 | 9/2011 | Vinci et al. | | |
| 2013/0289291 | A1 | 10/2013 | Nair et al. | | |

FOREIGN PATENT DOCUMENTS

| | | | |
|---|---|---|---|
| FR | 2374290 | | 7/1978 |
| WO | 2012/040175 | | 3/2012 |
| WO | WO-2012/030398 | A1 | 3/2012 |
| WO | WO-2012/036913 | A2 | 3/2012 |
| WO | WO2012030398 | A1 * | 3/2012 |
| WO | WO2012036913 | A2 * | 3/2012 |
| WO | WO-2013/002910 | A1 | 1/2013 |

OTHER PUBLICATIONS

Phillips et al., "Glycerides of Monnina Emarginata Seed Oil," *Biochimica et Biophysica Acta*, 218: 71-82 (1970).

International Search Report and Written Opinion for international application PCT/US2013/039139, mailed Oct. 1, 2013.

English-language abstract of FR 2374290 published Jul. 13, 1978.

European Search Report and Opinion for EP Application No. 13799879.5 dated Jun. 10, 2015.

"Synthesis and Evaluation of Esterified Estolide", url:http://shodhganga.inflibnet.ac.in/bitstream/10603/1471/11/11_chapter 5. Dec. 31, 2011.

Cermak, et al., "Synthesis and physical properties of estolides from lesquerella and castor fatty acid esters", Industrial Crops and Products, Elsevier, NL, vol. 23, No. 1, Jan. 1, 2006, 54-64.

* cited by examiner

*Primary Examiner* — Deborah D Carr
(74) *Attorney, Agent, or Firm* — Jeremy Forest

(57) ABSTRACT

Provided herein are processes of producing estolide base oils, including the process comprising providing at least one fatty acid ester, and contacting the at least one fatty acid ester with at least one fatty acid to form an estolide base oil. Exemplary processes include the use of transesterification to form the at least one fatty acid ester and/or estolide base oil.

24 Claims, No Drawings

PROCESSES OF PREPARING ESTOLIDE BASE OILS AND LUBRICANTS THAT INCLUDE TRANSESTERIFICATION

CROSS REFERENCE TO RELATED APPLICATIONS

This application claims the benefit under 35 U.S.C. §119 (e) of U.S. Provisional Patent Application No. 61/655,364, filed Jun. 4, 2012, which is incorporated herein by reference in its entirety for all purposes.

FIELD

The present disclosure relates to estolide base oil stocks and lubricants and methods of making the same. Exemplary processes include the use of transesterification.

BACKGROUND

Lubricant compositions typically comprise a base oil, such as a hydrocarbon base oil, and one or more additives. Estolides present a potential source of biobased, biodegradable oils that may be useful as lubricants and base stocks.

SUMMARY

Described herein are estolide compounds, estolide-containing compositions, and methods of making the same. In certain embodiments, such compounds and/or compositions may be useful as base oils and lubricants.

In certain embodiments, the estolides comprise at least one compound of Formula I:

Formula I

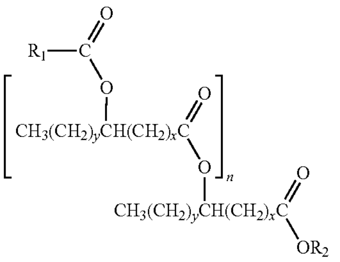

wherein x is, independently for each occurrence, an integer selected from 0, 1, 2, 3, 4, 5, 6, 7, 8, 9, and 10;

y is, independently for each occurrence, an integer selected from 0, 1, 2, 3, 4, 5, 6, 7, 8, 9, and 10;

n is an integer selected from 0, 1, 2, 3, 4, 5, 6, 7, 8, 9, 10, 11, and 12;

$R_1$ is an optionally substituted alkyl that is saturated or unsaturated, and branched or unbranched; and $R_2$ is an optionally substituted alkyl that is saturated or unsaturated, and branched or unbranched;

wherein each fatty acid chain residue of said at least one compound is independently optionally substituted.

In certain embodiments, the estolides comprise at least one compound of Formula II:

Formula II

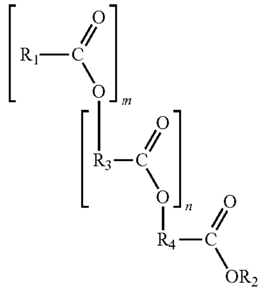

wherein m is an integer equal to or greater than 1;

n is an integer equal to or greater than 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments, the estolides comprise at least one estolide compound of Formula III:

Formula III

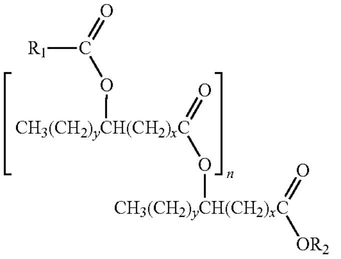

wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer equal to or greater than 0;

$R_1$ is an optionally substituted alkyl that is saturated or unsaturated, and branched or unbranched; and $R_2$ is an optionally substituted alkyl that is saturated or unsaturated, and branched or unbranched, wherein each fatty acid chain residue of said at least one compound is independently optionally substituted.

A process of producing an estolide base oil is also described. In certain embodiments, the process comprises:

providing at least one fatty acid ester; and contacting the at least one fatty acid ester with at least one fatty acid to provide an estolide base oil.

In certain embodiments, the process comprises:

providing at least one fatty acid ester;

transesterifying the at least one fatty acid ester with at least one alcohol to provide at least one second fatty acid ester; and contacting the at least one second fatty acid ester with at least one fatty acid to provide an estolide base oil.

DETAILED DESCRIPTION

The use of lubricants and lubricant-containing compositions may result in the dispersion of such fluids, compounds, and/or compositions in the environment. Petroleum base oils used in common lubricant compositions, as well as additives, are typically non-biodegradable and can be toxic. The present disclosure provides for the preparation and use of compositions comprising partially or fully bio-degradable base oils, including base oils comprising one or more estolides.

In certain embodiments, the compositions comprising one or more estolides are partially or fully biodegradable and thereby pose diminished risk to the environment. In certain embodiments, the compositions meet guidelines set for by the Organization for Economic Cooperation and Development (OECD) for degradation and accumulation testing. The OECD has indicated that several tests may be used to determine the "ready biodegradability" of organic chemicals. Aerobic ready biodegradability by OECD 301D measures the mineralization of the test sample to $CO_2$ in closed aerobic microcosms that simulate an aerobic aquatic environment, with microorganisms seeded from a waste-water treatment plant. OECD 301D is considered representative of most aerobic environments that are likely to receive waste materials. Aerobic "ultimate biodegradability" can be determined by OECD 302D. Under OECD 302D, microorganisms are pre-acclimated to biodegradation of the test material during a pre-incubation period, then incubated in sealed vessels with relatively high concentrations of microorganisms and enriched mineral salts medium. OECD 302D ultimately determines whether the test materials are completely biodegradable, albeit under less stringent conditions than "ready biodegradability" assays.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —$C(O)NH_2$ is attached through the carbon atom.

"Alkoxy" by itself or as part of another substituent refers to a radical —$OR^{31}$ where $R^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

The term "catalyst" refers to single chemical species; physical combinations of chemical species, such as mixtures, alloys, and the like; and combinations of one or more catalyst within the same region or location of a reactor or reaction vessel. Examples of catalyst include, e.g., Lewis acids, Bronsted acids, and Bismuth catalysts, wherein Lewis acids, Bronsted acids, and Bismuth catalysts may be single chemical species; physical combinations of chemical species, such as mixtures, alloys, and the like; and combinations of one or more catalyst within the same region or location of a reactor or reaction vessel.

"Compounds" refers to compounds encompassed by structural Formula I, II, and III herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I, II, and III include, but are not limited to, optical isomers of compounds of Formula I, II, and III, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I, II, and III cover all asymmetric variants of the compounds described herein, including isomers, racemates, enantiomers, diastereomers, and other mixtures thereof. In addition, compounds of Formula I, II and III include Z- and E-forms (e.g., cis- and trans-forms) of compounds with double bonds. The compounds of Formula I, II, and III may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated $\pi$ (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Solid-supported acid" refers to an acidic compound or material that is supported by or attached to another compound or material comprising a solid or semi-solid structure. Such materials include smooth supports (e.g., metal, glass, plastic, silicon, carbon (e.g., diamond, graphite, nanotubes, fullerenes (e.g., C-60)) and ceramic surfaces) as well as textured and porous materials such as clays and clay-like materials. Such materials also include, but are not limited to, gels, rubbers, polymers, and other non-rigid materials. Solid supports need not be composed of a single material. By way of example but not by way of limitation, a solid support may comprise a surface material (e.g. a layer or coating) and a different supporting material (e.g., coated glass, coated metals and plastics, etc.) In some embodiments, solid-supported acids comprise two or more different materials, e.g., in layers. Surface layers and coatings may be of any configuration and may partially or completely cover a supporting material. It is contemplated that solid supports may comprise any combination of layers, coatings, or other configurations of multiple materials. In some embodiments, a single material provides essentially all of the surface to which other material can be attached, while in other embodiments, multiple materials of the solid support are exposed for attachment of another material. Solid supports need not be flat. Supports include any type of shape including spherical shapes (e.g., beads). Acidic moieties attached to solid support may be attached to any portion of the solid support (e.g., may be attached to an interior portion of a porous solid support material). Exemplary solid-supported acids include, but are not limited to, cation exchange resins (e.g., Amberlyst®, Dowex®); acid-activated clays (e.g., montmorillonites); polymer-supported sulfonic acids (e.g., Nafion®); and silica-support catalysts (e.g., SPA-2).

"Substituted" refers to a group in which one or more hydrogen atoms are independently replaced with the same or different substituent(s). Examples of substituents include, but are not limited to, $—R^{64}$, $—R^{60}$, $—O^-$, —OH, =O, $—OR^{60}$, $—SR^{60}$, $—S^-$, =S, $—NR^{60}R^{61}$, $=NR^{60}$, —CN, $—CF_3$, —OCN, —SCN, —NO, $—NO_2$, $=N_2$, $—N_3$, $—S(O)_2O^-$, $—S(O)_2OH$, $—S(O)_2R^{60}$, $—OS(O_2)O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—C(S)OR^{60}$, $—NR^{62}C(O)NR^{60}R^{61}$, $—NR^{62}C(S)NR^{60}R^{61}$, $NR^{62}C(NR^{63})NR^{60}R^{61}$, $—C(NR^{62})NR^{60}R^{61}$, $—S(O)_2$, $NR^{60}R^{61}$, $—NR^{63}S(O)_2R^{60}$, $—NR^{63}C(O)R^{60}$, and $—S(O)R^{60}$;

wherein each $—R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, —O-haloalkyl, $-alkyl-NH_2$, alkoxy, cycloalkyl, cycloalkylalkyl, heterocycloalkyl, heterocycloalkylalkyl, aryl, heteroaryl, arylalkyl, heteroarylalkyl, $—O^-$, —OH, =O, —O-alkyl, —O-aryl, —O-heteroarylalkyl, —O-cycloalkyl, —O-heterocycloalkyl, —SH, $—S^-$, =S, —S-alkyl, —S-aryl, —S-heteroarylalkyl, —S-cycloalkyl, —S-heterocycloalkyl, $—NH_2$, =NH, —CN, $—CF_3$, —OCN, —SCN, —NO, $—NO_2$, $=N_2$, $—N_3$, $—S(O)_2O^-$, $—S(O)_2$, $—S(O)_2OH$, $—OS(O_2)O^-$, $—SO_2(alkyl)$, $—SO_2(phenyl)$, $—SO_2(haloalkyl)$, $—SO_2NH_2$, $—SO_2NH(alkyl)$, $—SO_2NH(phenyl)$, $—P(O)(O^-)_2$, $—P(O)(O-alkyl)(O^-)$, —OP(O)(O-alkyl)(O-alkyl), $—CO_2H$, —C(O)O(alkyl), —CON(alkyl)(alkyl), —CONH(alkyl), $—CONH_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

The term "fatty acid" refers to any natural or synthetic carboxylic acid comprising an alkyl chain that may be saturated, monounsaturated, or polyunsaturated, and may have straight or branched chains. The fatty acid may also be substituted. "Fatty acid," as used herein, includes short chain alkyl carboxylic acid including, for example, acetic acid, propionic acid, etc.

The term "fatty acid ester" refers to any composition comprising at least one ester of a fatty acid. For example, in certain embodiments, a fatty acid ester may comprise a fatty acid alkyl ester (e.g., 2-ethylhexyl oleate, methyl stearate, 9-dodecenoic acid methyl ester), wherein the fatty acid residue and the alkyl residue are independently branched or unbranched, and saturated or unsaturated. For example, in certain embodiments, the fatty acid ester may be derived from a process that includes the transesterification of an unsaturated fatty acid glyceride, such as a high-oleic vegetable oil (i.e., vegetable oil having a fatty acid profile of at least 70% oleic acid), with a monoalcohol such as isobutanol, to provide a fatty acid ester comprising an unsaturated fatty acid portion (i.e., oleic residue) and a saturated alkyl portion (i.e., isobutyl residue). Accordingly, in certain embodiments, forming a fatty acid ester via a process that includes the use of an unsubstituted, saturated monoalcohol will provide a fatty acid ester having an alkyl ester residue that is likewise unsubstituted and saturated. Alternatively, in certain embodiments, the fatty acid ester may comprise a fatty acid glyceride, such as a triglyceride. Unless otherwise indicated, it should be understood that reference to a fatty acid ester that is "unsaturated" means that the fatty acid ester comprises at least one unsaturated fatty acid residue. For example, an "unsaturated" triglyceride would comprise at least one fatty acid residue having at least one site of unsaturation. Similarly, unless stated otherwise, it should be understood that reference to an "unsaturated" fatty acid ester, prepared via a process that includes the transesterification of a first fatty acid ester with a monoalcohol, means that the fatty acid residue of the resulting fatty acid ester is unsaturated, while the alkyl ester portion provided by the monoalcohol may or may not be unsaturated.

The term "acid-activated clay" refers to clays that are derived from the naturally occurring ore bentonite or the mineral montmorillonite and includes materials prepared by calcination, washing or leaching with mineral acid, ion exchange or any combination thereof, including materials which are often called montmorillonites, acid-activated montmorillonites and activated montmorillonites. In certain embodiments, these clays may contain Bronsted as well as Lewis acid active sites with many of the acidic sites located within the clay lattice. Such clays include, but are not limited to the materials denoted as montmorillonite K10, montmorillonite clay, clayzic, clayfen, the Engelhardt series of catalysts related to and including X-9107, X9105, Girdler KSF, Tonsil and K-catalysts derived from montmorillonite, including but not limited to K5, K10, K20 and K30, KSF, KSF/O, and KP10. Other acid-activated clays may include X-9105 and X-9107 acid washed clay catalysts marketed by Engelhard.

The term "zeolite" refers to mesoporous aluminosilicates of the group IA or group IIA elements and are related to montmorillonite clays that are or have been acid activated. Zeolites may comprise what is considered an "infinitely" extending framework of $AlO_4$ and $SiO_4$ tetrahedra linked to each other by the sharing of oxygens. The framework structure may contain channels or interconnecting voids that are occupied by cations and water molecules. Acidic character may be imparted or enhanced by ion exchange of the cations, such as with ammonium ions and subsequent thermal deamination or calcination. The acidic sites may primarily be located within the lattice pores and channels. In certain instances, zeolites include, but are not limited to, the beta-type zeolites as typified by CP814E manufactured by Zeolyst International, the mordenite form of zeolites as typified by CBV21A manufactured by Zeolyst International, the Y-type zeolites as typified by CBV-720 manufactured by Zeolyst International, and the ZSM family of zeolites as typified by ZSM-5, and ZSM-11.

All numerical ranges herein include all numerical values and ranges of all numerical values within the recited range of numerical values.

The present disclosure relates to estolide compounds, compositions and methods of making the same. In certain embodiments, the present disclosure also relates to estolide compounds, compositions comprising estolide compounds, the synthesis of such compounds, and the formulation of such compositions. In certain embodiments, the present disclosure relates to biosynthetic estolides having desired viscometric properties, while retaining or even improving other properties such as oxidative stability and pour point. In certain embodiments, new methods of preparing estolide compounds exhibiting such properties are provided. The present disclosure also relates to compositions comprising certain estolide compounds exhibiting such properties.

In certain embodiments, the estolides comprise at least one compound of Formula I:

Formula I

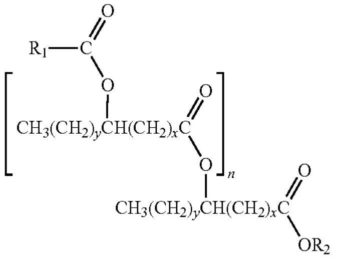

wherein x is, independently for each occurrence, an integer selected from 0, 1, 2, 3, 4, 5, 6, 7, 8, 9, and 10;

y is, independently for each occurrence, an integer selected from 0, 1, 2, 3, 4, 5, 6, 7, 8, 9, and 10;

n is an integer selected from 0, 1, 2, 3, 4, 5, 6, 7, 8, 9, 10, 11, and 12;

$R_1$ is an optionally substituted alkyl that is saturated or unsaturated, and branched or unbranched; and $R_2$ is an optionally substituted alkyl that is saturated or unsaturated, and branched or unbranched;

wherein each fatty acid chain residue of said at least one compound is independently optionally substituted.

In certain embodiments, the estolides comprise at least one compound of Formula II:

Formula II

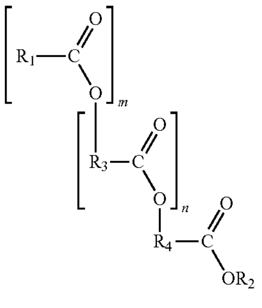

wherein m is an integer equal to or greater than 1;

n is an integer equal to or greater than 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments, the estolides comprise at least one estolide compound of Formula III:

Formula III

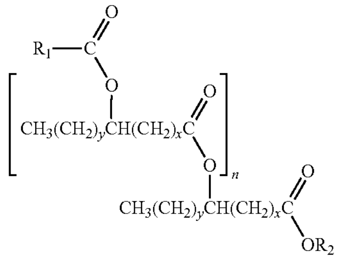

wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer equal to or greater than 0;

$R_1$ is an optionally substituted alkyl that is saturated or unsaturated, and branched or unbranched; and $R_2$ is an optionally substituted alkyl that is saturated or unsaturated, and branched or unbranched;

wherein each fatty acid chain residue of said at least one compound is independently optionally substituted.

In certain embodiments, the composition comprises at least one estolide of Formula I, II, or III where $R_1$ is hydrogen.

The terms "chain" or "fatty acid chain" or "fatty acid chain residue," as used with respect to the estolide compounds of Formula I, II, and III, refer to one or more of the fatty acid residues incorporated in estolide compounds, e.g., $R_3$ or $R_4$ of Formula II, or the structures represented by $CH_3(CH_2)_yCH(CH_2)_xC(O)O$— in Formula I and III.

The $R_1$ in Formula I, II, and III at the top of each Formula shown is an example of what may be referred to as a "cap" or "capping material," as it "caps" the top of the estolide. Similarly, the capping group may be an organic acid residue of general formula —OC(O)-alkyl, i.e., a carboxylic acid with a substituted or unsubstituted, saturated or unsaturated, and/or branched or unbranched alkyl as defined herein, or a formic acid residue. In certain embodiments, the "cap" or "capping group" is a fatty acid. In certain embodiments, the capping group, regardless of size, is substituted or unsubstituted, saturated or unsaturated, and/or branched or unbranched. The cap or capping material may also be referred to as the primary or alpha (α) chain.

Depending on the manner in which the estolide is synthesized, the cap or capping group alkyl may be the only alkyl from an organic acid residue in the resulting estolide that is unsaturated. In certain embodiments, it may be desirable to use a saturated organic or fatty-acid cap to increase the overall saturation of the estolide and/or to increase the resulting estolide's stability. For example, in certain embodiments, it may be desirable to provide a method of providing a saturated capped estolide by hydrogenating an unsaturated cap using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

The $R_4C(O)O$— of Formula II or structure $CH_3(CH_2)_yCH(CH_2)_xC(O)O$— of Formula I and III serve as the "base" or "base chain residue" of the estolide. Depending on the manner in which the estolide is synthesized, the base organic acid or fatty acid residue may be the only residue that remains in its free-acid form after the initial synthesis of the estolide. However, in certain embodiments, in an effort to alter or improve the properties of the estolide, the free acid may be reacted with any number of substituents. For example, it may be desirable to react the free acid estolide with alcohols, glycols, amines, or other suitable reactants to provide the corresponding ester, amide, or other reaction products. The base or base chain residue may also be referred to as tertiary or gamma (γ) chains.

The $R_3C(O)O$— of Formula II or structure $CH_3(CH_2)_yCH(CH_2)_xC(O)O$— of Formula I and III are linking residues that link the capping material and the base fatty-acid residue together. There may be any number of linking residues in the estolide, including when n=0 and the estolide is in its dimer form. Depending on the manner in which the estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta (β) chains.

In certain embodiments, the cap is an acetyl group, the linking residue(s) is one or more fatty acid residues, and the base chain residue is a fatty acid residue. In certain embodiments, the linking residues present in an estolide differ from one another. In certain embodiments, one or more of the linking residues differs from the base chain residue.

As noted above, in certain embodiments, suitable unsaturated fatty acids for preparing the estolides may include any mono- or polyunsaturated fatty acid. For example, monounsaturated fatty acids, along with a suitable catalyst, will form a single carbocation that allows for the addition of a second fatty acid, whereby a single link between two fatty acids is formed. Suitable monounsaturated fatty acids may include, but are not limited to, palmitoleic acid (16:1), vaccenic acid (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5). In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

The process for preparing the estolide compounds described herein may include the use of any natural or synthetic fatty acid source. However, it may be desirable to source the fatty acids from a renewable biological feedstock. For example, suitable starting materials of biological origin include, but are not limited to, plant fats, plant oils, plant waxes, animal fats, animal oils, animal waxes, fish fats, fish oils, fish waxes, algal oils and mixtures of two or more thereof. Other potential fatty acid sources include, but are not limited to, waste and recycled food-grade fats and oils, fats, oils, and waxes obtained by genetic engineering, fossil fuel-based materials and other sources of the materials desired.

In some embodiments, the estolide comprises fatty-acid chains of varying lengths. In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, y is, independently for each occurrence, an integer selected from 0, 1, 2, 3, 4, 5, 6, 7, 8, 9, 10, 11, 12, 13, 14, 15, 16, 17, 18, 19, and 20.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y is 15. In some embodiments, x+y is, independently for each chain, an integer selected from 6, 7, 8, 9, 10, 11, 12, 13, 14, 15, 16, 17, 18, 19, 20, 21, 22, 23, and 24.

In some embodiments, the estolide compound of Formula I, II, or III may comprise any number of fatty acid residues to form an "n-mer" estolide. For example, the estolide may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 1, wherein said at least one compound of Formula I, II, or III comprises the trimer. In some embodiments, n is greater than 1. In some embodiments, n is an integer selected from 0, 1, 2, 3, 4, 5, 6, 7, 8, 9, 10, 11, 12, 13, 14, 15, 16, 17, 18, 19, and 20.

In some embodiments, $R_1$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_1$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_1$ is selected from $C_{13}$ to $C_{17}$ alkyl, such as from $C_{13}$ alkyl, $C_{15}$ alkyl, and $C_{17}$ alkyl. In some embodiments, $R_1$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_2$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_3$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_3$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_3$ is selected from $C_{13}$ to $C_{17}$ alkyl, such as from $C_{13}$ alkyl, $C_{15}$ alkyl, and $C_{17}$ alkyl. In some embodiments, $R_3$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_4$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_4$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_4$ is selected from $C_{13}$ to $C_{17}$ alkyl, such as from $C_{13}$ alkyl, $C_{15}$ alkyl, and $C_{17}$ alkyl. In some embodiments, $R_4$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

As noted above, in certain embodiments, it may be possible to manipulate one or more of the estolides' properties by altering the length of $R_1$ and/or its degree of saturation. However, in certain embodiments, the level of substitution on $R_1$ may also be altered to change or even improve the estolides' properties. Without being bound to any particular theory, in certain embodiments, it is believed that the presence of polar substituents on $R_1$, such as one or more hydroxy groups, may increase the viscosity of the estolide, while increasing pour point. Accordingly, in some embodiments, $R_1$ will be unsubstituted or optionally substituted with a group that is not hydroxyl.

In some embodiments, the estolide is in its free-acid form, wherein $R_2$ of Formula I, II, or III is hydrogen. In some embodiments, $R_2$ is selected from optionally substituted alkyl that is saturated or unsaturated, and branched or unbranched. In certain embodiments, the $R_2$ residue may comprise any desired alkyl group, such as those derived from esterification of the estolide with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, in certain embodiments, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl. Such groups at the $R_2$ position may be derived from esterification of the free-acid estolide using the Jarcol™ line of alcohols marketed by Jarchem Industries, Inc. of Newark, N.J., including Jarcol™ I-18CG, I-20, I-12, I-16, I-18T, and 85BJ. In some cases, $R_2$ may be sourced from certain alcohols to provide branched alkyls such as isostearyl and isopalmityl. It should be understood that such isopalmityl and isostearyl alkyl groups may cover any branched variation of $C_{16}$ and $C_{18}$, respectively. For example, the estolides described herein may comprise highly-branched isopalmityl or isostearyl groups at the $R_2$ position, derived from the Fineoxocol® line of isopalmityl and isostearyl alcohols marketed by Nissan Chemical America Corporation of Houston, Tex., including Fineoxocol® 180, 180N, and 1600. Without being bound to any particular theory, in certain embodiments, large, highly-branched alkyl groups (e.g., isopalmityl and isostearyl) at the $R_2$ position of the estolides can provide at least one way to increase an estolide-containing composition's viscosity, while substantially retaining or even reducing its pour point.

In some embodiments, the compounds described herein may comprise a mixture of two or more estolide compounds of Formula I, II, and III. It is possible to characterize the chemical makeup of an estolide, a mixture of estolides, or a composition comprising estolides, by using the compound's, mixture's, or composition's measured estolide number (EN) of compound or composition. The EN represents the average number of fatty acids added to the base fatty acid. The EN also represents the average number of estolide linkages per molecule:

$$EN=n+1$$

wherein n is the number of secondary (β) fatty acids. Accordingly, a single estolide compound will have an EN that is a whole number, for example for dimers, trimers, and tetramers:

dimer EN=1 trimer EN=2 tetramer EN=3

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions may comprise a mixture of two or more estolides having an EN that is an integer or fraction of an integer that is greater than 4.5, or even 5.0. In some embodiments, the EN may be an integer or fraction of an integer selected from about 1.0 to about 5.0. In some embodiments, the EN is an integer or fraction of an integer selected from 1.2 to about 4.5. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6 and 5.8. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0, 5.2, 5.4, 5.6, 5.8, and 6.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. For example, in some embodiments the estolides described herein may comprise at least one compound of Formula II:

Formula II

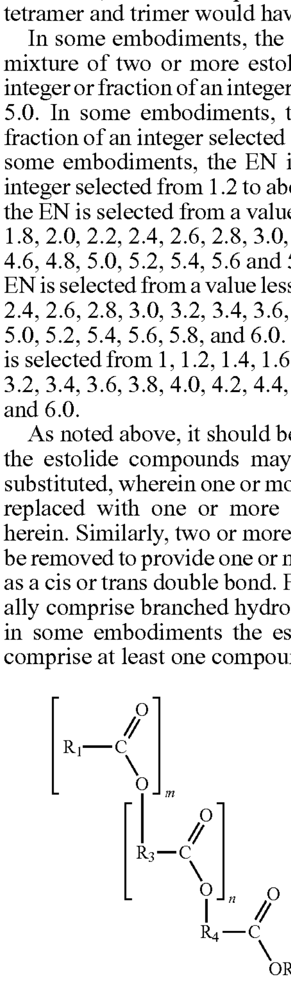

wherein m is an integer equal to or greater than 1;

n is an integer equal to or greater than 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments, m is 1. In some embodiments, m is an integer selected from 2, 3, 4, and 5. In some embodiments, n is an integer selected from 1, 2, 3, 4, 5, 6, 7, 8, 9, 10, 11, and 12. In some embodiments, one or more $R_3$ differs from one or more other $R_3$ in a compound of Formula II. In some embodiments, one or more $R_3$ differs from $R_4$ in a compound of Formula II. In some embodiments, if the compounds of Formula II are prepared from one or more polyunsaturated fatty acids, it is possible that one or more of $R_3$ and $R_4$ will have one or more sites of unsaturation. In some embodiments, if the compounds of Formula II are prepared from one or more branched fatty acids, it is possible that one or more of $R_3$ and $R_4$ will be branched.

In some embodiments, $R_3$ and $R_4$ can be $CH_3(CH_2)_yCH(CH_2)_x$—, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both $R_3$ and $R_4$ are $CH_3(CH_2)_yCH(CH_2)_x$—, the compounds may be compounds according to Formula I and III.

Without being bound to any particular theory, in certain embodiments, altering the EN produces estolide-containing compositions having desired viscometric properties while substantially retaining or even reducing pour point. For example, in some embodiments the estolides exhibit a decreased pour point upon increasing the EN value. Accordingly, in certain embodiments, a method is provided for retaining or decreasing the pour point of an estolide base oil by increasing the EN of the base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil or a composition comprising two or more estolide compounds is accomplished by use of at least one of distillation, chromatography, membrane separation, phase separation, affinity separation, and solvent extraction. In some embodiments, the distillation takes place at a temperature and/or pressure that is suitable to separate the estolide base oil or a composition comprising two or more estolide compounds into different "cuts" that individually exhibit different EN values. In some embodiments, this may be accomplished by subjecting the base oil or a composition comprising two or more estolide compounds to a temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

In some embodiments, estolide compounds and compositions exhibit an EN that is greater than or equal to 1, such as an integer or fraction of an integer selected from about 1.0 to about 2.0. In some embodiments, the EN is greater than or equal to 1.5, such as an integer or fraction of an integer selected from about 1.8 to about 2.8. In some embodiments, the EN is greater than or equal to about 4, such as an integer or fraction of an integer selected from about 4.0 to about 5.0. In some embodiments, the EN is greater than or equal to about 5, such as an integer or fraction of an integer selected from about 5.0 to about 6.0. In some embodiments, the EN is greater than or equal to 2, such as an integer or fraction of an integer selected from about 2.8 to about 3.8.

Typically, base stocks and estolide-containing compositions exhibit certain lubricity, viscosity, and/or pour point characteristics. For example, in certain embodiments, the base oils, compounds, and compositions may exhibit viscosities that range from about 10 cSt to about 250 cSt at 40° C., and/or about 3 cSt to about 30 cSt at 100° C. In some embodiments, the base oils, compounds, and compositions may exhibit viscosities within a range from about 50 cSt to about 150 cSt at 40° C., and/or about 10 cSt to about 20 cSt at 100° C.

In some embodiments, estolide compounds and compositions may exhibit desirable low-temperature pour point properties. In some embodiments, the estolide compounds and compositions may exhibit a pour point lower than about −10° C., about −15° C., about −25° C., about −35° C., −40° C., or even about −50° C. In some embodiments, the estolide compounds and compositions have a pour point of about −25° C. to about −45° C.

In addition, in certain embodiments, the estolides may exhibit decreased Iodine Values (IV) when compared to estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of estolides in an effort to increase the oil's oxidative stability, while also decreasing harmful deposits and the corrosiveness of the oil.

In some embodiments, estolide compounds and compositions described herein have an IV of less than about 40 cg/g or less than about 35 cg/g. In some embodiments, estolides have an IV of less than about 30 cg/g, less than about 25 cg/g, less than about 20 cg/g, less than about 15 cg/g, less than about 10 cg/g, or less than about 5 cg/g. The IV of a composition may be reduced by decreasing the estolide's degree of unsaturation. This may be accomplished by, for example, by increasing the amount of saturated capping materials relative to unsaturated capping materials when synthesizing the estolides. Alternatively, in certain embodiments, IV may be reduced by hydrogenating estolides having unsaturated caps.

In certain embodiments, the estolides described herein may be prepared from naturally or non-naturally occurring fatty acid esters. In certain embodiments, the fatty acid ester may be a fatty acid glyceride, such as a triglyceride, or may be derived from a fatty acid glyceride by a process that includes, for example, transesterification with an alcohol. In certain embodiments, the estolides are prepared through the process comprising:

providing at least one fatty acid ester; and contacting the at least one fatty acid ester with at least one fatty acid to form an estolide base oil.

In certain embodiments, the least one fatty acid ester is a fatty acid alkyl ester, such as one prepared via the transesterification of a fatty acid glyceride with a monoalcohol. Unless stated otherwise, it should be understood that a fatty acid alkyl ester comprises a fatty acid residue and an alkyl residue. For example, 2-ethylhexyl oleate comprises an unsaturated fatty acid portion (i.e., oleic residue) and a saturated alkyl portion (i.e., 2-ethylhexyl residue). Thus, in certain embodiments, the at least one fatty acid alkyl ester is unsaturated, wherein at least one fatty acid residue of the fatty acid alkyl ester comprises at least one site of unsaturation (e.g., monounsaturated). In certain embodiments the at least one fatty acid alkyl ester is unsubstituted, wherein the fatty acid residue and/or the alkyl residue lack substituents. In certain embodiments, the process of forming the estolide base oil includes forming a covalent bond between an oxygen of a carboxylic group of the at least one fatty acid and a carbon of at least one site of unsaturation of the at least one fatty acid ester.

In certain embodiments, the at least one fatty acid ester is contacted with at least one saturated fatty acid. For example, in certain embodiments, an unsubstituted fatty acid alkyl ester (e.g., 2-ethylhexyl oleate) is contacted with a saturated fatty acid (e.g., octanoic acid), wherein the resulting estolide base oil comprises a fully-saturated estolide dimer. In certain embodiments, contacting the at least one fatty acid ester with the at least one fatty acid occurs in the presence of at least one catalyst. Suitable catalysts may include any of the oligomerization catalysts described in further detail below. For example, in certain embodiments, the at least one catalyst is a Lewis acid, such as a triflate catalyst. In certain embodiments, the at least one catalyst is a Bronsted acid, such as triflic acid.

Alternatively, in certain embodiments, the at least one fatty acid ester is a glyceride. For example, in certain embodiments, the at least one fatty acid ester is a fatty acid triglyceride having at least one fatty acid residue with at least one site of unsaturation. Accordingly, in certain embodiments, contacting the fatty acid glyceride with at least one fatty acid will provide an estolide glyceride, also known as an "esto-glyceride". In certain embodiments, transesterification of the esto-glyceride with at least one alcohol will provide an esterified estolide. However, in certain embodiments, transesterification with an unbranched, short-chained alcohol (e.g., methanol or ethanol) may result in transesterification of both the glycerine ester linkage and the estolide ester linkage of the esto-glyceride. Thus, in certain embodiments, transesterification of the esto-glyceride is effected by a branched and/or bulky alcohol, such as 2-ethylhexanol. Without being bound to any particular theory, it is believed that reacting the esto-glyceride with a bulky and/or branched alcohol will limit transesterification to the glycerine ester linkages of the esto-glyceride, leaving the more sterically-hindered estolide ester linkages intact. Exemplary methods of preparing such compounds are set forth below in Schemes 5 and 6.

As noted above, in certain embodiments, the at least one fatty acid ester may be derived from a process that includes transesterification. Accordingly, in certain embodiments, the estolide base oil is prepared through the process comprising:

providing at least one first fatty acid ester;

transesterifying the at least one first fatty acid ester with at least one alcohol to provide at least one second fatty acid ester; and contacting the at least one second fatty acid ester with at least one fatty acid to form an estolide base oil.

In certain embodiments, the at least one first fatty acid ester is a glyceride, such as a monoglyceride, diglyceride, or triglyceride. In certain embodiments, the transesterifying is conducted with an alcohol, such as a monoalcohol (e.g., methanol), diol (e.g., 1,3-propanediol), or a polyol (e.g., 1,2,4-butanediol). In certain embodiments, the transesterifying may be accomplished using any suitable methods known by persons of skill in the art, including those used in the preparation of biodiesel, such as methods using acid-catalyzed and/or Lewis Acid-catalyzed conditions. In certain embodiments, the transesterification may take place in the presence of thermal or microwave radiation, with or without the presence of a catalyst.

In certain embodiments, the process of producing an estolide base oil comprises contacting a fatty acid ester with a fatty acid in the presence of a catalyst, wherein the resulting estolide base oil comprises an esterified estolide. In certain embodiments, the catalyst comprises one or more compounds selected from Bronsted acid catalysts and Lewis acid catalysts. In certain embodiments, the Lewis acid catalyst is selected from one or more triflates (trifluormethanesulfonates) such as transition metal triflates and lanthanide triflates. Suitable triflates may include, but are not limited to, AgOTf (silver triflate), $Cu(OTf)_2$ (copper triflate), NaOTf (sodium triflate), $Fe(OTf)_2$ (iron (II) triflate), $Fe(OTf)_3$ (iron (III) triflate), LiOTf (lithium triflate), $Yb(OTf)_3$ (ytterbium triflate), $Y(OTf)_3$ (yttrium triflate), $Zn(OTf)_2$ (zinc triflate), $Ni(OTf)_2$ (nickel triflate), $Bi(OTf)_3$ (bismuth triflate), $La(OTf)_3$ (lanthanum triflate), and $Sc(OTf)_3$ (scandium triflate). In certain embodiments, the Lewis acid catalyst is $Fe(OTf)_3$. In certain embodiments, the Lewis acid catalyst is $Bi(OTf)_3$. In certain embodiments, the Lewis acid catalyst is $Fe(OTf)_2$.

In certain embodiments, the Lewis acid catalyst comprises one or compounds selected from metal compounds, such as iron compounds, cobalt compounds, and nickel compounds. In certain embodiments, the metal compound is selected from one or more of $FeX_n$ (n=2, 3), $Fe(CO)_5$, $Fe_3(CO)_{12}$, $Fe(CO)_3(ET)$, $Fe(CO)_3(DE)$, $Fe(DE)_2$, $CpFeX(CO)_2$, $[CpFe(CO)_2]_2$, $[Cp^*Fe(CO)_2]_2$, $Fe(acac)_3$, $Fe(OAc)_n$ (n=2, 3), $CoX_2$, $CO_2(CO)_8$, $Co(acac)_n$, (n=2, 3), $Co(OAc)_2$, $CpCO(CO)_2$, $Cp^*Co(CO)_2$, $NiX_2$, $Ni(CO)_4$, $Ni(DE)_2$, $Ni(acac)_2$, and $Ni(OAc)_2$, wherein X is selected from hydrogen, halogen, hydroxyl, cyano, alkoxy, carboxylato, and thiocyanato; wherein Cp is a cyclopentadienyl group; acac is an acetylacetonato group; DE is selected from norbornadienyl, 1,5-cyclooctadienyl, and 1,5-hexadienyl; ET is selected from ethylenyl and cyclooctenyl; and OAc represents an acetate group. In some embodiments, the Lewis acid is an iron compound. In some embodiments, the Lewis acid is an iron compound selected from one or more of $Fe(acac)_3$, $FeCl_3$, $Fe_2(SO_4)_3$, $Fe_2O_3$, and $FeSO_4$.

In addition, or in the alternative, the catalyst comprises the use of one or more Bronsted acid catalysts. Exemplary Bronsted acids include, but are not limited to, hydrochloric acid, nitric acid, sulfamic acid, methylsulfamic acid, methanesulfonic acid, sulfuric acid, phosphoric acid, perchloric acid, triflic acid, p-toluenesulfonic acid (p-TsOH), and combinations thereof. In certain embodiments, the Bronsted acid is selected from one or more of sulfamic acid and methylsulfamic acid. In some embodiments, the Bronsted acid may comprise cation exchange resins, acid exchange resins and/or solid-supported acids. Such materials may include styrene-divinylbenzene copolymer-based strong cation exchange resins such as Amberlyst® (Rohm & Haas; Philadelphia, Pa.), Dowex® (Dow; Midland, Mich.), CG resins from Resintech, Inc. (West Berlin, N.J.), and Lewatit resins such as MonoPlus™ S 100H from Sybron Chemicals Inc. (Birmingham, N.J.). Exemplary solid acid catalysts include cation exchange resins, such as Amberlyst® 15, Amberlyst® 35, Amberlite® 120, Dowex® Monosphere M-31, Dowex® Monosphere DR-2030, and acidic and acid-activated mesoporous materials and natural clays such a kaolinites, bentonites, attapulgites, montmorillonites, and zeolites. Exemplary catalysts also include organic acids supported on mesoporous materials derived from polysaccharides and activated carobon, such as Starbon®-supported sulphonic acid catalysts (University of York) like Starbon® 300, Starbon® 400, and Starbon® 800. Phosphoric acids on solid supports may also be suitable, such as phosphoric acid supported on silica (e.g., SPA-2 catalysts sold by Sigma-Aldrich).

In certain embodiments, one or more fluorinated sulfonic acid polymers may be used as solid-acid catalysts for the processes described herein. These acids are partially or totally fluorinated hydrocarbon polymers containing pendant sulfonic acid groups, which may be partially or totally converted to the salt form. Exemplary sulfonic acid polymers include Nafion® perfluorinated sulfonic acid polymers such as Nafion® SAC-13 (E.I. du Pont de Nemours and Company, Wilmington, Del.). In certain embodiments, the catalyst comprises a Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton ($H^+$), or the metal salt form. In some embodiments, the process comprises use of one or more of protic or aprotic catalysts.

In some embodiments, the formation of the estolide base oil is aided by the application of electromagnetic energy. In certain embodiments, the electromagnetic energy used to aid the process is microwave electromagnetic energy. In certain embodiments, for example, application of electromagnetic radiation may be applied to reduce the overall reaction time and improve the yield of estolide by conducting the reaction in a microwave reactor in the presence of a catalyst. In some embodiments, reacting the at least one fatty acid ester with the at least fatty acid is conducted in the presence of a catalyst (e.g., a Lewis acid) and microwave radiation. In some embodiments, the reaction is conducted in a microwave reactor with $Bi(OTf)_3$. In some embodiments, the reaction is conducted in a microwave reactor with $Fe(OTf)_3$. In some embodiments, the reaction is conducted in a microwave reactor with $Fe(OTf)_2$.

In some embodiments, depending on the nature of the catalyst and the reaction conditions, it may be desirable to carry out the process at a certain temperature and/or pressure. In some embodiments, for example, suitable temperatures for effecting estolide formation may equal to or less than about 50° C. In certain embodiments, suitable temperatures may include temperatures greater than about 50° C., such as a range of about 50° C. to about 100° C. In some embodiments, the estolide formation is carried out at about 60° C. to about 80° C. In some embodiments, the estolide formation is carried out, for at least a portion of the time, at about 50° C., about 52° C., about 54° C., about 56° C., about 58° C., about 60° C., about 62° C., about 64° C., about 66° C., about 68° C., about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., and about 100° C. In some embodiments, the estolide formation is carried out, for at least a period of time, at a temperature of no greater than about 52° C., about 54° C., about 56° C., about 58° C., about 60° C., about 62° C., about 64° C., about 66° C., about 68° C., about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., or about 100° C.

In some embodiments, suitable conditions may include reactions that are carried out at a pressure of about 1 atm abs (absolute), or less than 1 atm abs, such at less than about 250 torr abs, less than about 100 torr abs, less than about 50 torr abs, or less than about 25 torr abs. In some embodiments, estolide formation is carried out at a pressure of about 1 torr abs to about 20 torr abs, or about 5 torr abs to about 15 torr abs. In some embodiments, estolide formation, for at least a period of time, is carried out at a pressure of greater than about 5, about 10, about 15, about 20, about 25, about 30, about 35, about 40, about 45, out 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, and about 250 torrs abs. In some embodiments, estolide formation, for at least a period of time, is carried out at a pressure of less than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, or about 250 torrs abs.

The present disclosure further relates to methods of making estolides according to Formula I, II, and III. By way of example, the reaction of an unsaturated fatty acid with an organic acid and the esterification of the resulting free acid estolide are illustrated and discussed in the following Schemes 1 and 2. The preparation of fatty acid esters via transesterification is exemplified in Scheme 3, while the formation of estolides from fatty acid esters and free fatty acids is exemplified in Scheme 4. The particular structural formulas used to illustrate the reactions correspond to those for synthesis of compounds according to Formula I and III; however, the methods apply equally to the synthesis of compounds according to Formula II, with use of compounds having structure corresponding to $R_3$ and $R_4$ with a reactive site of unsaturation.

As illustrated below, compound 100 represents an unsaturated fatty acid that may serve as the basis for preparing the estolide compounds described herein.

Scheme 1

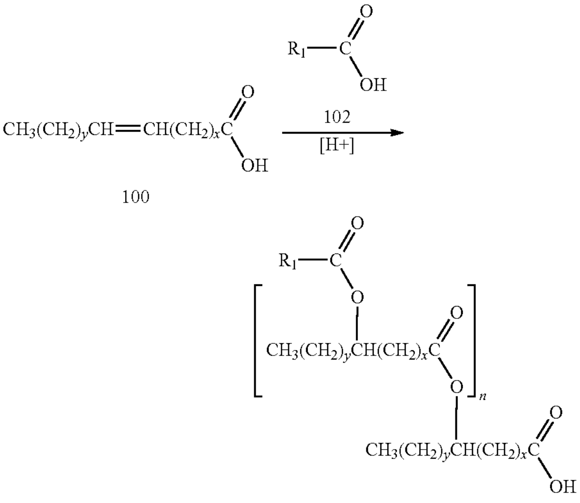

100

104

In Scheme 1, wherein x is, independently for each occurrence, an integer selected from 0 to 20, y is, independently for each occurrence, an integer selected from 0 to 20, n is an integer greater than or equal to 1, and $R_1$ is an optionally substituted alkyl that is saturated or unsaturated, and branched or unbranched, unsaturated fatty acid 100 may be combined with compound 102 and a proton from a proton source to form free acid estolide 104. In certain embodiments, compound 102 is not included, and unsaturated fatty acid 100 may be exposed alone to acidic conditions to form free acid estolide 104, wherein $R_1$ would represent an unsaturated alkyl group. In certain embodiments, if compound 102 is included in the reaction, $R_1$ may represent one or more optionally substituted alkyl residues that are saturated or unsaturated and branched or unbranched. Any suitable proton source may be implemented to catalyze the formation of free acid estolide 104, including but not limited to homogenous acids and/or strong acids like hydrochloric acid, sulfuric acid, perchloric acid, nitric acid, triflic acid, and the like.

Scheme 2

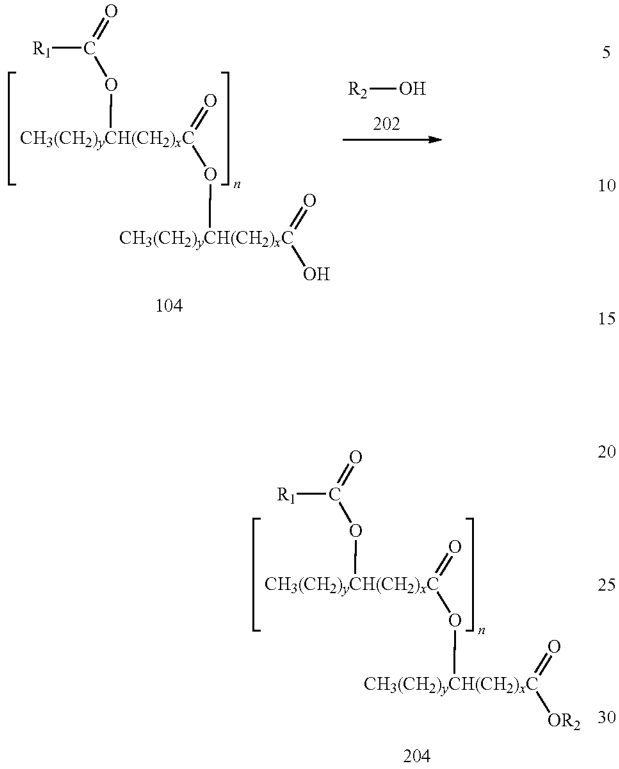

Similarly, in Scheme 2, wherein x is, independently for each occurrence, an integer selected from 0 to 20, y is, independently for each occurrence, an integer selected from 0 to 20, n is an integer greater than or equal to 1, and $R_1$ and $R_2$ are each an optionally substituted alkyl that is saturated or unsaturated, and branched or unbranched, free acid estolide 104 may be esterified by any suitable procedure known to those of skilled in the art, such as acid-catalyzed reduction with alcohol 202, to yield esterified estolide 204. Other exemplary methods may include other types of Fischer esterification, such as those using Lewis acid catalysts such as $BF_3$.

Scheme 3

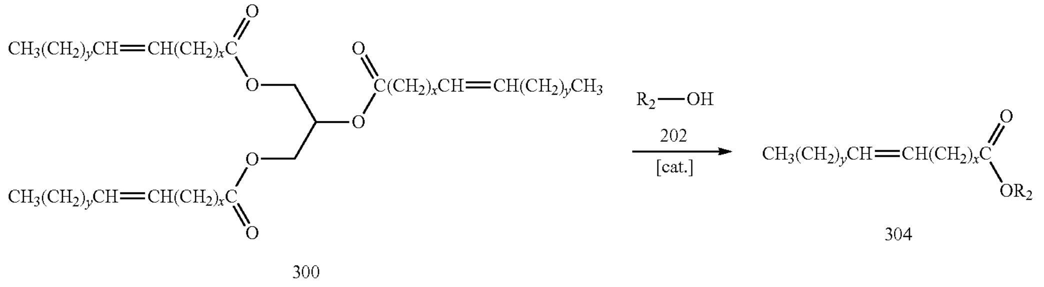

In Scheme 3, wherein x is, independently for each occurrence, an integer selected from 0 to 20, y is, independently for each occurrence, an integer selected from 0 to 20, and $R_2$ is an optionally substituted alkyl that is saturated or unsaturated, and branched or unbranched, triglyceride 300 may be transesterified by any suitable catalyst known to those of skilled in the art, such as acid-catalyzed reduction with alcohol 202, to yield fatty acid alkyl ester 304.

Scheme 4

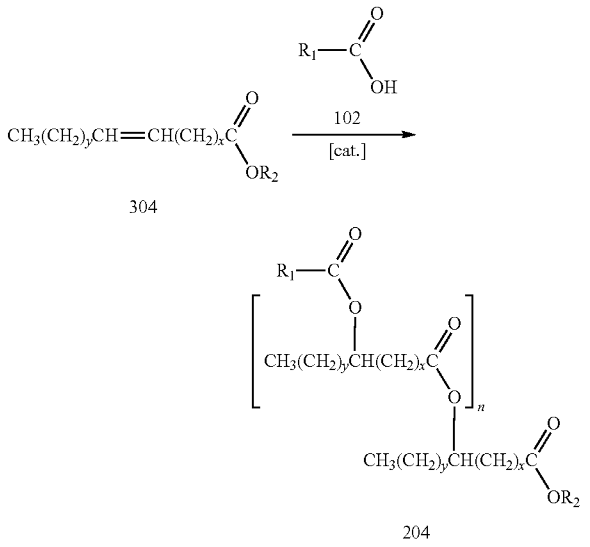

In Scheme 4, wherein x is, independently for each occurrence, an integer selected from 0 to 20, y is, independently for each occurrence, an integer selected from 0 to 20, n is an integer greater than or equal to 0, and $R_1$ and $R_2$ are independently selected from optionally substituted alkyl that is saturated or unsaturated, and branched or unbranched, unsaturated fatty acid alkyl ester 304 may be combined with compound 102 and a catalyst to form esterified estolide 104. In certain embodiments, $R_1$ of compound 102 is saturated and, thus, is not capable of undergoing further oligomerization. Accordingly, in certain embodiments, the reaction set forth in Scheme 4 forms primarily dimer estolides, wherein n=0. Any suitable catalyst source may be implemented to catalyze the formation of esterified estolide 204, including but not limited to homogenous acids and/or strong acids like hydrochloric acid, sulfuric acid, methanesulfonic acid, perchloric acid, nitric acid, triflic acid, and the like. Other exemplary catalysts may include Lewis acid catalysts such as those previously described herein.

Scheme 5

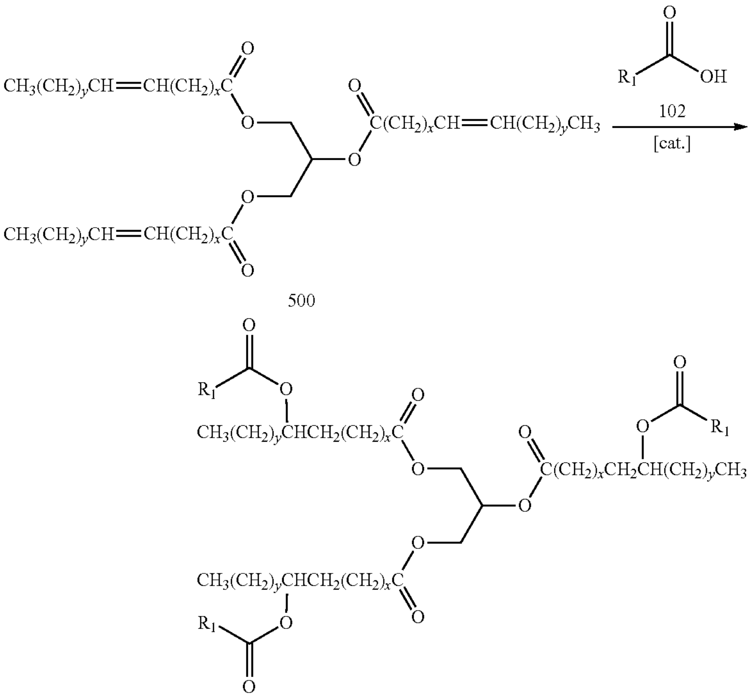

500

504

In Scheme 5, wherein x is, independently for each occurrence, an integer selected from 0 to 20, y is, independently for each occurrence, an integer selected from 0 to 20, and $R_1$ is independently selected from optionally substituted alkyl that is saturated or unsaturated, and branched or unbranched, unsaturated triglyceride 500 may be combined with fatty acid 102 under catalytic conditions to form esto-triglyceride 504. In certain embodiments, $R_1$ of compound 102 is saturated and, thus, is not capable of undergoing further oligomerization. Any suitable catalyst source may be implemented to catalyze the formation of esto-triglyceride 504, including but not limited to Lewis acid catalysts such as those described herein.

Scheme 6

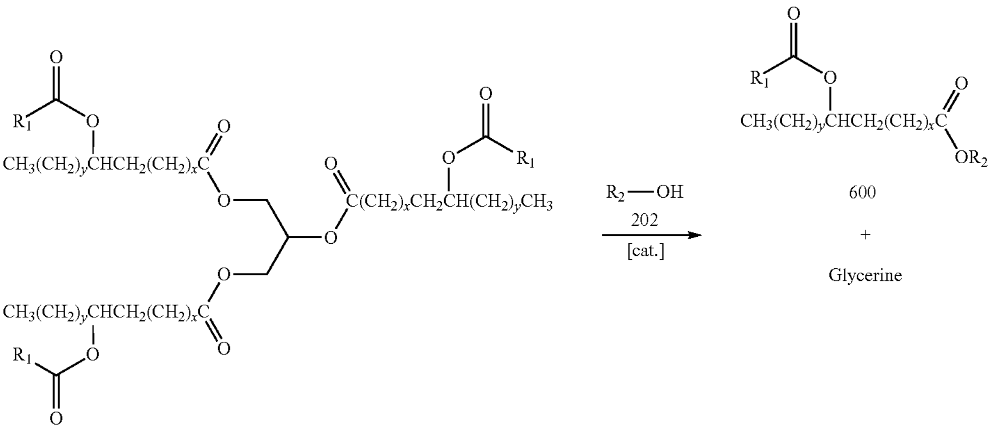

504

In Scheme 6, wherein x is, independently for each occurrence, an integer selected from 0 to 20, y is, independently for each occurrence, an integer selected from 0 to 20, and $R_2$ is an optionally substituted alkyl that is saturated or unsaturated, and branched or unbranched, esto-triglyceride 504 may be transesterified by any suitable catalyst known to those of skilled in the art, such as acid-catalyzed reduction with alcohol 202, to yield esterified estolide 600 and glycerine.

As discussed above, in certain embodiments, the estolides described herein may have improved properties which render them useful as base stocks for biodegradable lubricant applications. Such applications may include, without limitation, crankcase oils, gearbox oils, hydraulic fluids, drilling fluids, two-cycle engine oils, greases, and the like. Other suitable uses may include marine applications, where biodegradability and toxicity are of concern. In certain embodiments, the nontoxic nature of certain estolides described herein may also make them suitable for use as lubricants in the cosmetic and food industries.

In certain embodiments, the estolide compounds may meet or exceed one or more of the specifications for certain end-use applications, without the need for conventional additives. For example, in certain instances, high-viscosity lubricants, such as those exhibiting a kinematic viscosity of greater than about 120 cSt at 40° C., or even greater than about 200 cSt at 40° C., may be desired for particular applications such as gearbox or wind turbine lubricants. Prior-known lubricants with such properties typically also demonstrate an increase in pour point as viscosity increases, such that prior lubricants may not be suitable for such applications in colder environments. However, in certain embodiments, the counterintuitive properties of certain compounds described herein (e.g., increased EN provides estolides with higher viscosities while retaining, or even decreasing, the oil's pour point) may make higher-viscosity estolides particularly suitable for such specialized applications.

Similarly, the use of prior-known lubricants in colder environments may generally result in an unwanted increase in a lubricant's viscosity. Thus, depending on the application, it may be desirable to use lower-viscosity oils at lower temperatures. In certain circumstances, low-viscosity oils may include those exhibiting a viscosity of lower than about 50 cSt at 40° C., or even about 40 cSt at 40° C. Accordingly, in certain embodiments, the low-viscosity estolides described herein may provide end users with a suitable alternative to high-viscosity lubricants for operation at lower temperatures.

In some embodiments, it may be desirable to prepare lubricant compositions comprising an estolide base stock. For example, in certain embodiments, the estolides described herein may be blended with one or more additives selected from polyalphaolefins, synthetic esters, polyalkylene glycols, mineral oils (Groups I, II, and III), pour point depressants, viscosity modifiers, anti-corrosives, antiwear agents, detergents, dispersants, colorants, antifoaming agents, and demulsifiers. In addition, or in the alternative, in certain embodiments, the estolides described herein may be co-blended with one or more synthetic or petroleum-based oils to achieve desired viscosity and/or pour point profiles. In certain embodiments, certain estolides described herein also mix well with gasoline, so that they may be useful as fuel components or additives.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance:

NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1$H NMR by a peak at about 4.84 ppm.

Estolide Number (EN):

The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV):

The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I, II, and III, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value:

The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC):

GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC:

To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation:

To prepare the samples, 10 mg of estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation:

The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation:

The iodine value is estimated by the following equation based on ASTM Method D97 (ASTM International, Conshohocken, Pa.):

$$IV = \sum 100 \times \frac{A_f \times MW_I \times db}{MW_f}$$

$A_f$=fraction of fatty compound in the sample $MW_I$=253.81, atomic weight of two iodine atoms added to a double bond db=number of double bonds on the fatty compound $MW_f$=molecular weight of the fatty compound The properties of exemplary estolide compounds and compositions described herein are identified in the following examples and tables.

Other Measurements:

Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat#244252) and heated to 60° C. in vacuo (10 torr abs) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (μ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 1). Certain data are reported below in Tables 1 and 8.

Example 2

The acid catalyst reaction was conducted in a 50 gallon Pfaudler RT-Series glass-lined reactor. Oleic acid (50 Kg, OL 700, Twin Rivers) and whole cut coconut fatty acid (18.754 Kg, TRC 110, Twin Rivers) were added to the reactor with 70% perchloric acid (1145 mL, Aldrich Cat#244252) and heated to 60° C. in vacuo (10 torr abs) for 24 hrs while continuously being agitated. After 24 hours the vacuum was released. 2-Ethylhexanol (34.58 Kg) was then added to the reactor and the vacuum was restored. The reaction was allowed to continue under the same conditions (60° C., 10 torr abs) for 4 more hours. At which time, KOH (744.9 g) was dissolved in 90% ethanol/water (5000 mL, 90% EtOH by volume) and added to the reactor to quench the acid. The solution was then allowed to cool for approximately 30 minutes. The contents of the reactor were then pumped through a 1μ filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 2). Certain data are reported below in Tables 2 and 7.

Example 3

The estolides produced in Example 1 (Ex. 1) were subjected to distillation conditions in a Myers 15 Centrifugal Distillation still at 300° C. under an absolute pressure of approximately 12 microns (0.012 torr). This resulted in a primary distillate having a lower EN average (Ex. 3A), and a distillation residue having a higher EN average (Ex. 3B). Certain data are reported below in Table 1.

TABLE 1

| Estolide Base Stock | EN | Pour Point (° C.) | Iodine Value (cg/g) |
|---|---|---|---|
| Ex. 3A | 1.35 | −32 | 31.5 |
| Ex. 1 | 2.34 | −40 | 22.4 |
| Ex. 3B | 4.43 | −40 | 13.8 |

Example 4

Estolides produced in Example 2 (Ex. 2) were subjected to distillation conditions in a Myers 15 Centrifugal Distillation still at 300° C. under an absolute pressure of approximately 12 microns (0.012 torr). This resulted in a primary distillate having a lower EN average (Ex. 4A), and a distillation residue having a higher EN average (Ex. 4B). Certain data are reported below in Table 2.

TABLE 2

| Estolide Base Stock | EN | Pour Point (° C.) | Iodine Value (cg/g) |
|---|---|---|---|
| Ex. 4A | 1.31 | −30 | 13.8 |
| Ex. 2 | 1.82 | −33 | 13.2 |
| Ex. 4B | 3.22 | −36 | 9.0 |

Example 5

Estolides of Formula I, II, and III are prepared according to the method set forth in Examples 1 and 2, except that the 2-ethylhexanol esterifying alcohol is replaced with various other alcohols. Alcohols to be used for esterification include those identified in Table 3 below. Esterifying alcohols to be used, including those listed below, may be saturated or unsaturated, and branched or unbranched, or substituted with one or more alkyl groups selected from methyl, ethyl, propyl, isopropyl, butyl, isobutyl, sec-butyl, tert-butyl, pentyl, isopentyl, neopentyl, hexyl, isohexyl, and the like, to form a branched or unbranched residue at the $R_2$ position. Examples of combinations of esterifying alcohols and $R_2$ Substituents are set forth below in Table 3:

TABLE 3

| Alcohol | $R_2$ Substituents |
|---|---|
| $C_1$ alkanol | methyl |
| $C_2$ alkanol | ethyl |
| $C_3$ alkanol | n-propyl, isopropyl |
| $C_4$ alkanol | n-butyl, isobutyl, sec-butyl |
| $C_5$ alkanol | n-pentyl, isopentyl neopentyl |
| $C_6$ alkanol | n-hexyl, 2-methyl pentyl, 3-methyl pentyl, 2,2-dimethyl butyl, 2,3-dimethyl butyl |
| $C_7$ alkanol | n-heptyl and other structural isomers |
| $C_8$ alkanol | n-octyl and other structural isomers |
| $C_9$ alkanol | n-nonyl and other structural isomers |
| $C_{10}$ alkanol | n-decanyl and other structural isomers |
| $C_{11}$ alkanol | n-undecanyl and other structural isomers |
| $C_{12}$ alkanol | n-dodecanyl and other structural isomers |
| $C_{13}$ alkanol | n-tridecanyl and other structural isomers |
| $C_{14}$ alkanol | n-tetradecanyl and other structural isomers |
| $C_{15}$ alkanol | n-pentadecanyl and other structural isomers |
| $C_{16}$ alkanol | n-hexadecanyl and other structural isomers |
| $C_{17}$ alkanol | n-heptadecanyl and other structural isomers |
| $C_{18}$ alkanol | n-octadecanyl and other structural isomers |
| $C_{19}$ alkanol | n-nonadecanyl and other structural isomers |
| $C_{20}$ alkanol | n-icosanyl and other structural isomers |
| $C_{21}$ alkanol | n-heneicosanyl and other structural isomers |
| $C_{22}$ alkanol | n-docosanyl and other structural isomers |

Example 6

Under a nitrogen atmosphere, 2-ethylhexyl oleate (1 equiv), lauric acid (6 equiv), and triflic acid (0.25 equiv) were added to glass reaction vessel equipped with stir bar. The reaction mixture was heated to 60° C. and stirred for 24 hrs. After allowing the reaction vessel to cool to room temperature, the crude reaction product was then washed with water and brine. The washed reaction product was then dried over sodium sulfate, filtered, and distilled to provide the estolide product.

Example 7

Under a nitrogen atmosphere, a glass reaction vessel is charged with high-oleic soybean oil (Vistive® Gold, 1 equiv.), 2-ethylhexanol (6 equiv), and triflic acid (0.5 equiv). The reaction mixture is heated to a temperature between 160-200° C. and stirred for a period of 6-10 hrs. After allowing the reaction vessel to cool to room temperature, the crude reaction product is washed with water and brine. The washed reaction product is then dried over sodium sulfate, filtered, and distilled to remove glycerine, providing 2-ethylhexanol monoesters that include 2-ethylhexyl oleate.

The invention claimed is:

1. A process of producing an estolide base oil comprising providing at least one unsaturated fatty acid glyceride;

transesterifying the at least one unsaturated fatty acid glyceride with at least one alcohol to provide at least one fatty acid alkyl ester having at least one site of unsaturation; and contacting the at least one fatty acid ester with at least one fatty acid in the presence of a catalyst to provide an estolide base oil, wherein the process of producing the estolide base oil includes forming a covalent bond between an oxygen of a carboxylic group of the at least one fatty acid and a carbon of the at least one site of unsaturation of the at least one fatty acid alkyl ester.

2. The process according to claim 1, wherein the at least one unsaturated fatty acid glyceride is a triglyceride.

3. The process according to claim 2, wherein the at least one unsaturated fatty acid glyceride is derived from a high-oleic vegetable oil.

4. The process according to claim 1, wherein the at least one alcohol is a monoalcohol.

5. The process according to claim 4, wherein the at least one alcohol is a branched or unbranched $C_6$-$C_{12}$ monoalcohol.

6. The process according to claim 5, wherein the at least one alcohol is 2-ethylhexanol.

7. The process according to claim 1, wherein the at least one fatty acid alkyl ester is monounsaturated.

8. The process according to claim 7, wherein the alkyl residue of the at least one fatty acid alkyl ester is saturated and branched.

9. The process according to claim 1, wherein the at least one fatty acid is saturated.

10. The process according to claim 9, wherein the at least one fatty acid is a $C_6$-$C_{14}$ fatty acid.

11. The process according to claim 1, wherein the at least one catalyst is a Lewis acid.

12. The process according to claim 11, wherein the at least one catalyst is a triflate.

13. The process according to claim 1, wherein the at least one catalyst is a Bronsted acid.

14. The process according to claim 13, wherein at least one catalyst is selected from one or more of hydrochloric acid, nitric acid, methanesulfonic acid, sulfuric acid, phosphoric acid, perchloric acid, triflic acid, or p-TsOH.

15. The process according to claim 1, wherein the estolide base oil comprises at least one compound selected from compounds of Formula I:

Formula I

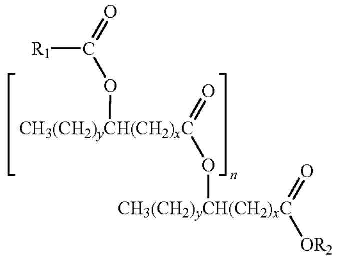

wherein x is, independently for each occurrence, an integer selected from 0 to 20;

y is, independently for each occurrence, an integer selected from 0 to 20;

n is an integer greater than or equal to 0;

$R_1$ is an optionally substituted alkyl that is saturated or unsaturated, and branched or unbranched; and $R_2$ is an optionally substituted alkyl that is saturated or unsaturated, and branched or unbranched, wherein each fatty acid chain residue of said at least one compound is independently optionally substituted.

16. The composition according to claim 15, wherein x is, independently for each occurrence, an integer selected from 1 to 10;

y is, independently for each occurrence, an integer selected from 1 to 10;

n is an integer selected from 0 to 8;

$R_1$ is an optionally substituted $C_1$ to $C_{20}$ alkyl that is saturated or unsaturated, and branched or unbranched; and $R_2$ is an optionally substituted $C_1$ to $C_{20}$ alkyl that is saturated or unsaturated, and branched or unbranched, wherein each fatty acid chain residue is unsubstituted.

17. The process according to claim 16, wherein x+y is, independently for each chain, an integer selected from 13 to 15; and n is an integer selected from 0 to 6.

18. The process according to claim 15, wherein $R_2$ is unsubstituted.

19. The process according to claim 18, wherein $R_2$ is selected from $C_6$ to $C_{12}$ alkyl.

20. The process according to claim 19, wherein $R_2$ is 2-ethylhexyl.

21. The process according to claim 15, wherein $R_1$ is unsubstituted.

22. The process according to claim 21, wherein $R_1$ is selected from unsubstituted $C_7$ to $C_{17}$ alkyl that is unbranched and saturated or unsaturated.

23. The process according to claim 15, wherein x is, independently for each occurrence, an integer selected from 7 to 8.

24. The process according to claim 23, wherein y is, independently for each occurrence, an integer selected from 7 to 8.

* * * * *